US010418221B2

(12) United States Patent
Miller et al.

(10) Patent No.: US 10,418,221 B2
(45) Date of Patent: Sep. 17, 2019

(54) X-RAY SOURCE WITH TUBE-SHAPED FIELD-EMITTER

(71) Applicant: Moxtek, Inc., Orem, UT (US)

(72) Inventors: Eric Miller, Prove, UT (US); Bill Hansen, Genola, UT (US)

(73) Assignee: Moxtek, Inc., Orem, UT (US)

( * ) Notice: Subject to any disclaimer, the term of this patent is extended or adjusted under 35 U.S.C. 154(b) by 418 days.

(21) Appl. No.: 15/342,575

(22) Filed: Nov. 3, 2016

(65) Prior Publication Data
US 2017/0200580 A1 Jul. 13, 2017

Related U.S. Application Data

(60) Provisional application No. 62/275,985, filed on Jan. 7, 2016.

(51) Int. Cl.
| H01J 35/06 | (2006.01) |
| H01J 35/32 | (2006.01) |
| H01J 35/18 | (2006.01) |
| A61B 6/00 | (2006.01) |

(52) U.S. Cl.
CPC .............. H01J 35/065 (2013.01); *A61B 6/40* (2013.01); *H01J 35/186* (2019.05); *H01J 35/32* (2013.01)

(58) Field of Classification Search
CPC .... H01J 2235/086; H01J 35/065; H01J 35/08; H01J 35/18; H01J 35/064; H01J 35/112; H01J 35/116; H01J 35/186; H01J 35/32; H01J 2235/164; H01J 2235/18
See application file for complete search history.

(56) References Cited

U.S. PATENT DOCUMENTS

| 5,729,583 | A | * | 3/1998 | Tang | A61B 6/145 378/122 |
| 5,911,919 | A | * | 6/1999 | Billings | H01B 1/06 252/515 |
| 6,108,402 | A | * | 8/2000 | Chornenky | A61N 5/1001 378/119 |
| 6,324,257 | B1 | * | 11/2001 | Halavee | A61N 5/1001 378/121 |
| 2001/0009970 | A1 | * | 7/2001 | Chornenky | A61N 5/1001 600/3 |
| 2001/0019601 | A1 | * | 9/2001 | Tkahashi | B82Y 10/00 378/119 |
| 2003/0179854 | A1 | * | 9/2003 | Jaafar | A61N 5/1001 378/119 |
| 2005/0041780 | A1 | * | 2/2005 | Le-Pierrard | H01J 35/165 378/119 |
| 2006/0131588 | A1 | * | 6/2006 | Gruen | C23C 16/274 257/77 |

(Continued)

*Primary Examiner* — Chih-Cheng Kao
(74) *Attorney, Agent, or Firm* — Thorpe, North & Wester, LLP (57) ABSTRACT

An x-ray tube can include an electron-emitter, which can include a tube-shape with a minimum inside diameter of at least 0.5 millimeters. The electron-emitter can provide field-emission of electrons, and thus can avoid the electrical power required for heating, and can avoid degradation due to high temperature of, a thermionic-emission electron-emitter. This type of electron-emitter, with a tube-shape, can have a relatively large electron-emission region, allowing high electrical current without excessive current density.

20 Claims, 7 Drawing Sheets

(56) References Cited

U.S. PATENT DOCUMENTS

| | | | |
|---|---|---|---|
| 2007/0103841 A1* | 5/2007 | Lee | H05F 3/06 361/212 |
| 2011/0087062 A1* | 4/2011 | Hornig | H01J 35/065 600/3 |
| 2011/0188635 A1* | 8/2011 | Cho | H01J 35/06 378/122 |
| 2015/0071410 A1 | 3/2015 | Barnum et al. | |
| 2015/0303024 A1 | 10/2015 | Harker et al. | |

* cited by examiner

X-RAY SOURCE WITH TUBE-SHAPED FIELD-EMITTER

PRIORITY CLAIM

Priority is claimed to U.S. Provisional Patent Application Ser. No. 62/275,985, filed Jan. 7, 2016, which is hereby incorporated herein by reference.

FIELD OF THE INVENTION

The present application is related generally to x-ray sources.

BACKGROUND

In an x-ray tube, electrons can emit from an electron-emitter to an anode. A material in or on the anode can form x-rays in response to impinging electrons from the electron-emitter. An x-ray tube with a thermionic electron-emitter must expend a substantial amount of energy to heat the electron-emitter. This energy for heating the electron-emitter can be costly and can place an added burden on the energy source. It would be beneficial to reduce the required energy input to an x-ray tube.

Another problem of thermionic electron-emitters is evaporation of the filament because of its high temperature. Consequently, filament life can be reduced. Also, the evaporated metal from the filament can coat the x-ray tube in undesirable locations, and can create an electrically conductive path between the anode and the filament, resulting in degraded x-ray tube operation and/or early failure.

It is sometimes desirable to insert an x-ray tube into a small space. Because of large voltage differentials between the electron-emitter and the anode, it can be difficult to manufacture small x-ray tubes. It would be beneficial to provide an x-ray tube that can have a small size.

SUMMARY

It has been recognized that it would be advantageous to have an x-ray tube with an electron source that is both robust and requires relatively low energy input. It has been recognized that it would be advantageous to have a small x-ray tube. The present invention is directed to various embodiments of x-ray tubes that satisfy these needs. Each embodiment can satisfy one, some, or all of these needs.

The x-ray tube can comprise an electron-emitter, an anode, an x-ray window, and an evacuated-region between the electron-emitter and the anode. The electron-emitter can be electrically insulated from the anode. The anode can include a material for generation of x-rays in response to impinging electrons from the electron-emitter. The electron-emitter can be capable of field-emission of electrons; can include a tube-shape; can have an open-end facing the anode, with at least a portion of the evacuated-region located between the open-end and the anode; can include an electron-emission region, capable of emitting electrons to the anode, at an inside of the electron-emitter, or at the open-end of the electron-emitter, or both; and can include an electrically-conductive path from the electron-emission region to an electrical connection for a power-supply.

DEFINITIONS

As used herein, the term "electrostatic discharge" means a rapid flow of static electricity from one object to another object. Electrostatic discharge can result in damage to electronic components.

As used herein, the term "electrostatic dissipation," and similar phrases such as "dissipate the electrostatic charge," mean a relatively slower flow of electricity from one object to another object. Electrostatic dissipation usually does not result in damage to electronic components.

As used herein, the term "evacuated-region" means a region with a substantial vacuum, such as is typically used inside of x-ray tubes.

As used herein, the term "field-emission" means cold electronic emission or in other words the emission of electrons due to an electrical-field without a necessity of heating the electron-emitter.

As used herein, the term "height of the cone" means a distance from a circular base of the cone to its point.

As used herein, the term "tube-shaped" means a shape that is elongated and hollow, but may or may not be cylindrical in shape.

DETAILED DESCRIPTION

Figure 1:
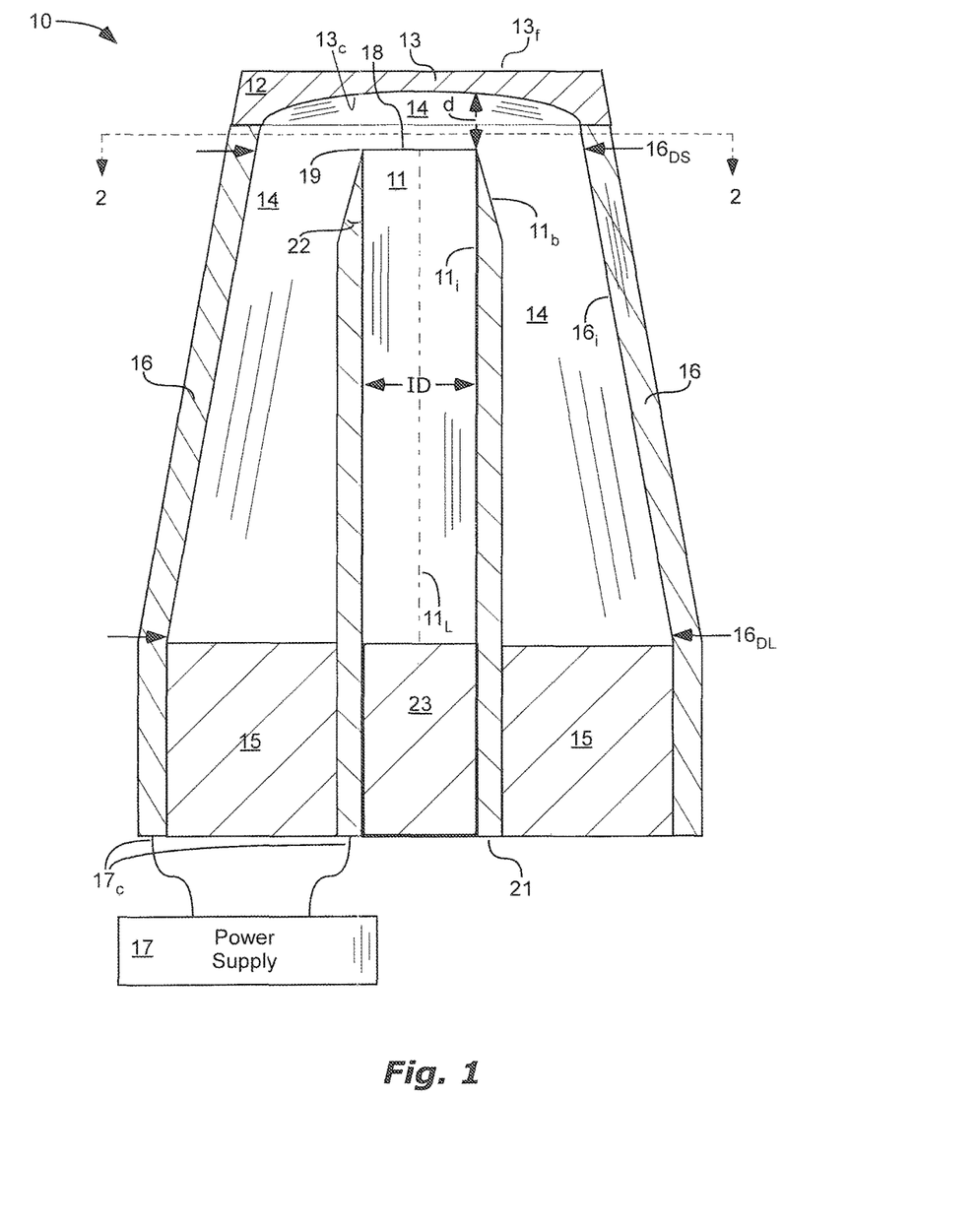
FIG. 1 is a schematic, cross-sectional side-view of a transmission-target x-ray tube 10 with a tube-shaped electron-emitter 11, and a power supply 17, in accordance with an embodiment of the present invention.
Figure 2:
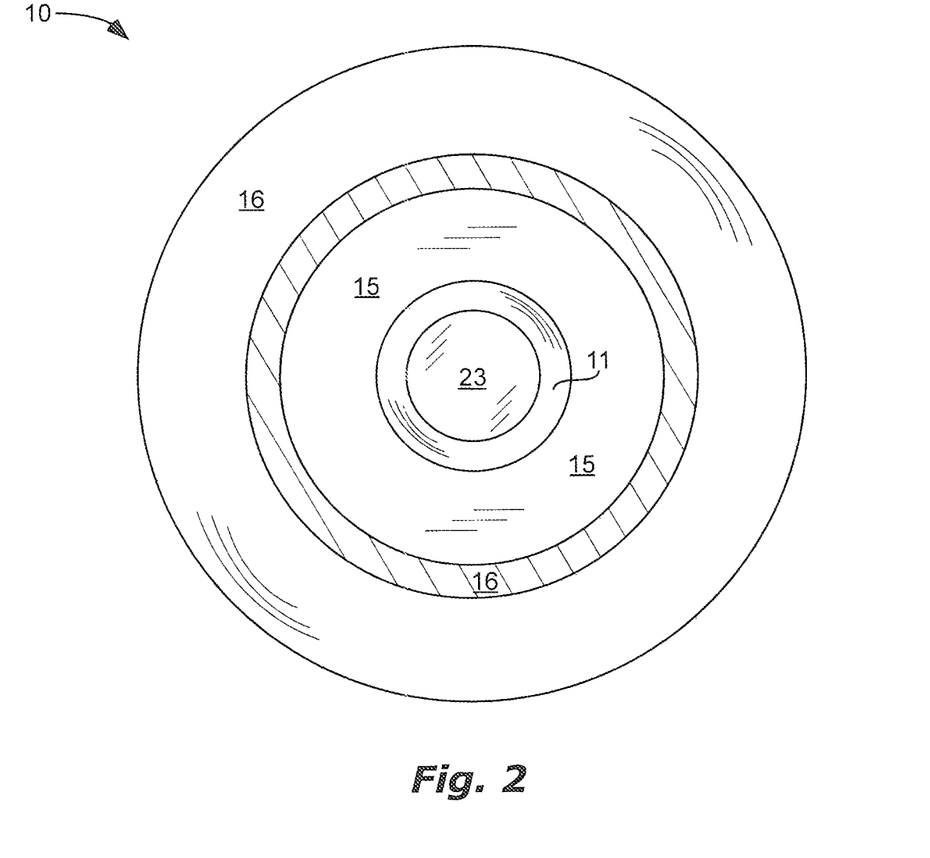
FIG. 2 is a schematic, cross-sectional top-view of the x-ray tube 10 of FIG. 1, taken along line 2-2 in FIG. 1, in accordance with an embodiment of the present invention.

As illustrated in FIGS. 1-2, an x-ray tube 10 is shown comprising an electron-emitter 11, an anode 12, an x-ray window 13, and an evacuated-region 14 between the electron-emitter 11 and the anode 12. The anode 12 can include a material for generation of x-rays in response to impinging electrons from the electron-emitter 11. Such material is typically a high melting-point metal, such as for example chromium, gold, iron, cobalt, copper, molybdenum, silver, and tantalum. The evacuated-region 14 can have a low pressure, such as for example less than $1\times10^{-8}$ Torr in one aspect, less than $5\times10^{-9}$ Torr in another aspect, or less than $1\times10^{-9}$ Torr in another aspect.

The electron-emitter 11 can have a tube-shape. The tube-shape can be cylindrical or other shape with an open-end 18 and a hollow core. The electro emitter 11 can have an open-end 18 facing the anode 12 at a distal-end of the electron emitter closer to the anode 12. At least a portion of the evacuated-region 14 can be located between the open-end 18 and the anode 12. The electron-emitter 11 can have a proximal-end 21 opposite of the open-end 18. The open-end 18 of the electron-emitter 11 can be circular. In one embodiment, as shown in FIG. 1, the x-ray tube 10 can include only a single electron-emitter 11, and this single electron-emitter 11 can be a single tube extending along a single longitudinal-axis 13A.

The x-ray window 13 can include some or all of the properties (e.g. low deflection, high x-ray transmissivity, low visible and infrared light transmissivity) of the x-ray window described in U.S. patent application Ser. No. 14/597,955, filed on Jan. 15, 2015, which is incorporated herein by reference in its entirety. The x-ray window 13 can have a transmissivity of greater than 50% for x-rays having an energy of 1.74 keV.

The x-ray tube 10 can be electrically connected to a power supply 17 (e.g. by electrical connections 17c) forming an x-ray source. The power supply can provide a large voltage differential between the electron-emitter 11 and the anode 12, such as for example at least 1 kilovolt in one aspect, at least 4 kilovolts in another aspect, or at least 10 kilovolts in another aspect.

The x-ray tube 10 can be made in a way to allow field-emission of electrons from the electron-emitter 11. Field-emission of electrons can use less electrical power than thermionic-emission, by avoiding the need to heat a filament. The power supply 17 for a field-emitter x-ray tube 10 can also have a simpler, more compact design, because there is no need to provide alternating current for heating the filament, thus reducing power supply size and power supply design and manufacturing cost. Also, use of a cold electron-emitter 11, instead of a heated filament, can avoid problems of filament evaporation. The X-ray tube 10 can operate with the electron-emitter maintained at relatively low temperatures, such as less than 100° Celsius in one aspect or less than 50° Celsius in another aspect. The x-ray tube 10, with a tube-shaped electron-emitter 11 can be simple to manufacture, and can be made relatively small, allowing the x-ray tube 10 to be inserted into small locations.

A tube-shaped electron-emitter 11 can be better than a single-pointed (i.e. cone-shaped, like a sharpened pencil) electron-emitter because the tube-shape can have an increased area for electron emission. A single-pointed electron field emitter can wear down, due to a very high electric current density at its tip, thus potentially decreasing the life of the x-ray tube. The tube-shaped electron-emitter 11, in contrast, can have a larger electron-emission region, capable of emitting electrons to the anode 12. For example, the electron-emission region can have a surface area of at least 5 square millimeters in one aspect, at least 15 square millimeters in another aspect, or at least 30 square millimeters in another aspect. Thus, compared to a single-pointed electron field emitter, the tube-shaped electron-emitter 11 can have a lower electric current density for the same electric current, which can result in increased life of the x-ray tube 10. The electron-emission region can be at an inside 11, of the electron-emitter 11, or at the open-end 18 of the electron-emitter 11, or both.

The electron-emission region can include a coating for increasing production of electrons. The coating, or the electron-emitter 11 itself, can include one or more of the following: materials with low electron work function, thorium, barium oxide, a carbon-containing material, or combinations thereof. The carbon-containing material can include one or more of the following: graphene, graphene oxide, diamond, polycrystalline diamond, nanocrystalline diamond, and carbon nanotubes. The coating, or the electron-emitter 11 itself, can be doped, such as for example with arsenic, cesium, oxygen, barium, thorium, or combinations thereof.

The electron-emitter 11 can have a specified minimum inside diameter ID for ease of manufacturing and to allow a larger electron-emission region. The minimum inside diameter ID of the electron-emitter 11 can be at least 0.1 millimeters in one aspect, at least 0.5 millimeters in another aspect, at least 1 millimeter in another aspect, or at least 2 millimeters in another aspect.

Figure 3:
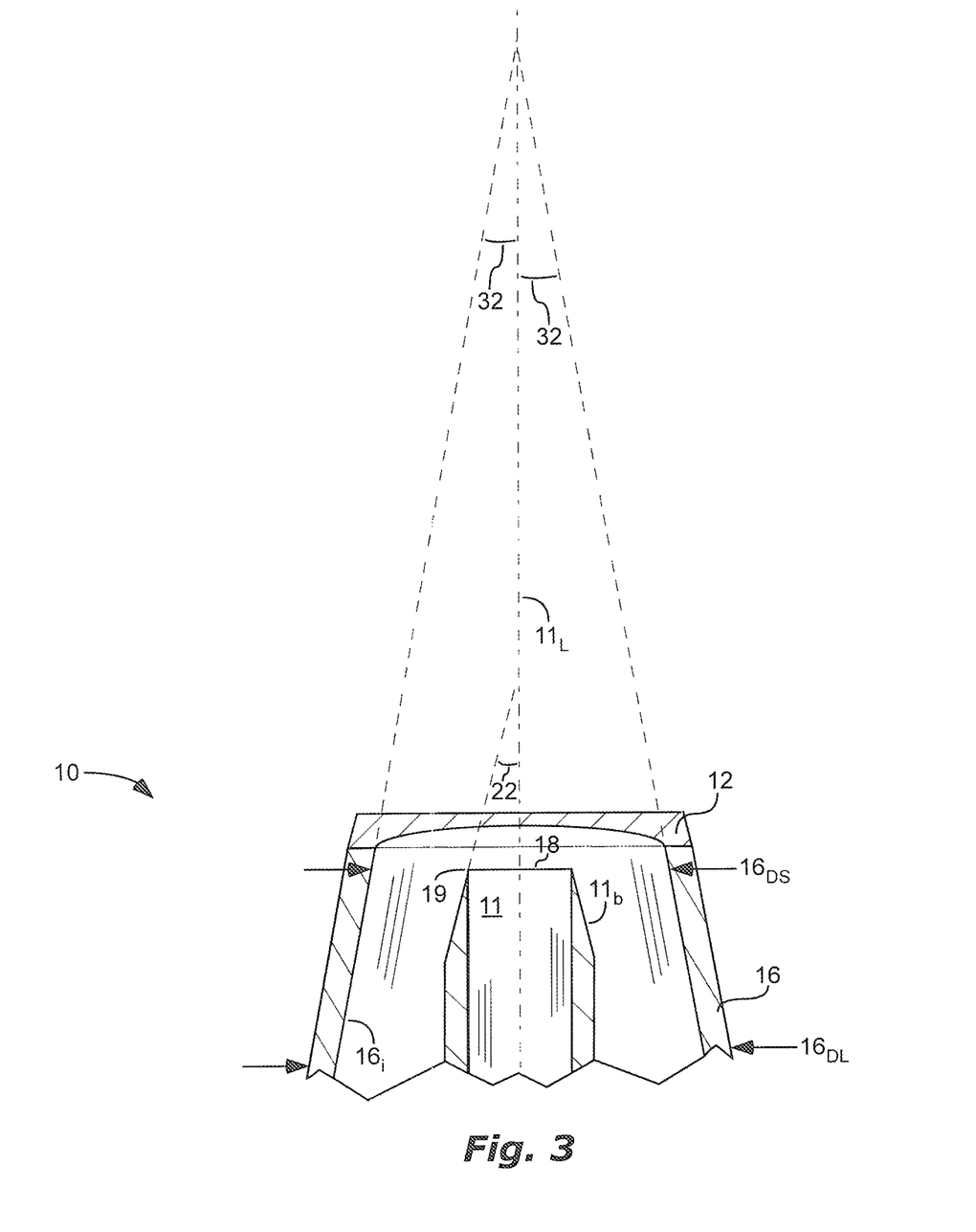
FIG. 3 is an expanded, schematic, cross-sectional side-view of a portion the x-ray tube 10 of FIG. 1, showing a taper-angle 32 of an inner-surface 16, of the enclosure 16 and an internal angle 22 of a pointed-edge 19 of the open-end 18 of the electron-emitter 11, in accordance with an embodiment of the present invention.

A large electric-field gradient between the open-end 18 of the electron-emitter and the anode 12 can allow field-emission of electrons. The electron-emitter 11 can have or can include a tube-shape, allowing a large electric-field gradient at its edge or rim. To increase the electric-field gradient, a cross-section of the open-end 18 of the electron-emitter 11 can be pointed and the open-end 18 can have a pointed-edge 19. Thus, the edge or rim of the electron-emitter 11 can be the pointed-edge. A sharp pointed edge can increase the electric-field gradient. An internal angle 22 of the pointed-edge 19 of the open-end 18 of the electron-emitter 11 can be less than 30 degrees in one aspect, less than 20 degrees in another aspect, or less than 12 degrees in another aspect, relative to a longitudinal-axis $11_L$ of the electron-emitter 11.

The pointed-edge 19 of the open-end 18 of the electron-emitter 11 can be made by grinding an edge of the tube-shaped electron-emitter. Thus, for ease of manufacturing, the pointed-edge 19 can have an exterior bevel $11_b$. In other words, the pointed edge 19 can be an edge at an inside diameter of the open-end 18 of the electron-emitter 11. The exterior bevel 11$_b$ of the pointed edge 19 can be linear.

The electric-field gradient between the open-end 18 of the electron-emitter 11 and the anode 12 can be increased by locating the open-end 18 close to the anode 12. For example, a distance d between the open-end 18 of the electron-emitter 11 and the anode 12 can be greater than 0.05 millimeters in one aspect or greater than 0.1 millimeters in another aspect, and less than and 1 millimeter in one aspect or less than 2 millimeters in another aspect.

An orientation between the open-end 18 of the electron-emitter 11 and the anode 12 can affect the electric-field gradient and a magnitude of the flux of electrons emitted from the electron-emitter 11 to the anode 12. For example, the open-end 18 can be substantially perpendicular to a longitudinal-axis 11$_L$ of the electron-emitter 11. Alternatively, the open-end 18 can have an oblique angle with respect to the a longitudinal-axis 11$_L$ of the electron-emitter 11, such as for example between 10° and 50° or between 45° and 75°.

The x-ray tube 10 can also have an enclosure 16. The enclosure 16 can be hermetically-sealed to the anode 12. The enclosure 16 can at least partially enclose the evacuated-region 14. The enclosure 16 can circumscribe all or at least a portion of the electron-emitter 11. The enclosure 16 can be electrically conductive and can serve as an electrically-conductive path from the anode 12 to the electrical connection 17$_c$ for the power supply 17.

In x-ray tubes with an electrically-insulative enclosure, such as glass or ceramic, small amounts of target material, knocked off of the target due to impinging electrons, can coat an inner surface 16$_i$ of the enclosure and can create an undesirable, electrically-conductive path from the anode to the cathode or electron-emitter. If an electrically-conductive enclosure 16 is use in the present x-ray tube design 10, this problem can be avoided. Any target material coating an inside of the enclosure 16 likely will not adversely affect x-ray tube 10 operation, because the enclosure is electrically conductive and is not relied upon to insulate the electron-emitter 11 from the anode 12. The electron-emitter 11 can be electrically insulated from the enclosure 16 by the evacuated-region 14 and by an insulating material 15 (e.g. glass or ceramic) between the electron-emitter 11 and the enclosure 16. This insulating material 15 can be located far from the target material on the anode 12 as shown in FIG. 1, and thus there is less chance of target material coating this insulating material 15 and causing a short circuit between the enclosure 16 and the electron-emitter 11.

As shown in FIGS. 1 and 3, the inner-surface 16$_i$ of the enclosure 16 can taper inward, with a smaller inside-diameter 16$_{DS}$ closer to the open-end 18 of the electron-emitter 11, and a larger inside-diameter 16$_{DL}$ closer to the proximal-end 21 of the electron-emitter 11, forming a taper-angle 32, in order to increase the electric-field gradient at the open-end 18 of the electron-emitter 11, and thus improve or allow field emission. Examples of the taper-angle 32 include greater than 1 degree in one aspect, greater than 2 degrees in another aspect, greater than 8 degrees in another aspect; and less than 10 degrees in one aspect, less than 20 degrees in another aspect, or less than 25 degrees in another aspect.

In a Spindt field emitter, or Spindt array, a gate electrode that surrounds the electron-emitter 11 can also be used to improve the electric-field gradient, but manufacturing can be difficult. The above options for improving the electric-field gradient can be used instead of this gate electrode. Avoiding the Spindt field emitter design can simplify the power supply 17, because the power supply 17 need only provide two bias voltages for the x-ray tube 10—one for the electron-emitter 11 and one for the anode 12.

Avoiding the Spindt field emitter design can simplify manufacturing because the gate electrode in a Spindt field emitter design may need to be very close to the electron emitter, such as about 1 micrometer for example. In contrast, in x-ray tube 10, a closest solid object to the electron-emitter 11 at the open-end 18, can be the anode 12. Another way of describing this is any straight-line-path from the electron-emitter to the enclosure 16, radially outward from the electron-emitter 11, perpendicular to a longitudinal-axis of the electron-emitter 11 along the distal-region of the electron emitter 11, extends only through the evacuated-region. The distal-region of the electron-emitter 11 is a portion of the electron-emitter 11 from the open-end 18 towards the proximal-end 21 for certain percent of a length L (see FIG. 5) of the electron-emitter 11, such, as 15% in one aspect, 25% in another aspect, or 50% in another aspect. A lowest voltage, radially outward from the electron-emitter 11 along the portion of the electron emitter in the distal-region can be at least 3000 volts greater than a voltage of the open-end 18 of the electron-emitter 11. In other words, radially outward from the electron-emitter 11, the first solid object can be the enclosure 16, which can be at ground potential, and thus several thousands of volts more positive than the electron-emitter 11.

X-ray tube 10 in FIG. 1 has a transmission-target, the anode 12 includes the x-ray window 13. The x-ray window 13 can have a concave-side 13$_c$ facing the electron-emitter 11. The concave-side 13$_c$ of the x-ray window 13 can include the material for generation of x-rays. This concave shape can improve the electric-field gradient. The concave shape can be manufactured by selecting a film of material (e.g. beryllium) with the desired thickness, then machining out the concave shape. The x-ray window 13 can include a substantially flat-side 13$_f$ that is outside of the x-ray tube 10 and opposite of the concave-side 13$_c$. This flat-side 13$_f$ can be used to bear against or support another object, such as the bottom-side of a flat-panel-display for example.

Figure 4A:
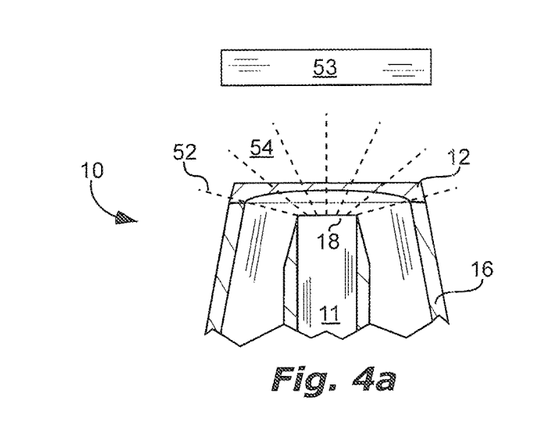
FIG. 4a is a schematic, cross-sectional side-view of a portion the x-ray tube 10 of FIG. 1, showing emission of x-rays 52 into a region-of-air 54 near a device 53 with an electrostatic charge, in accordance with an embodiment of the present invention.
Figure 4B:
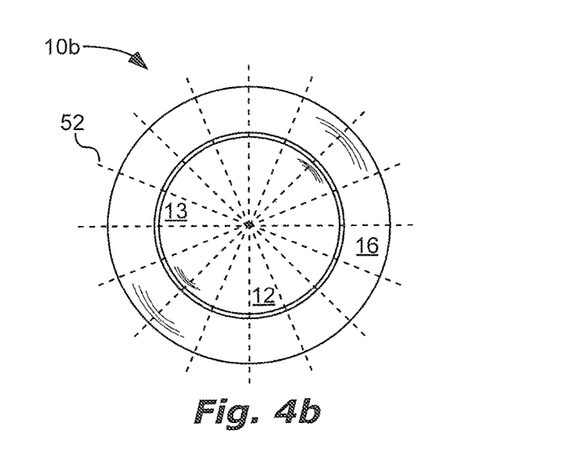
FIG. 4b is a schematic top-view of x-ray tube 10b, one embodiment of x-ray tube 10 of FIG. 1, showing emission of x-rays 52 in an approximately hemispherical or $2*\pi$ steradian shape, in accordance with an embodiment of the present invention.
Figure 4C:
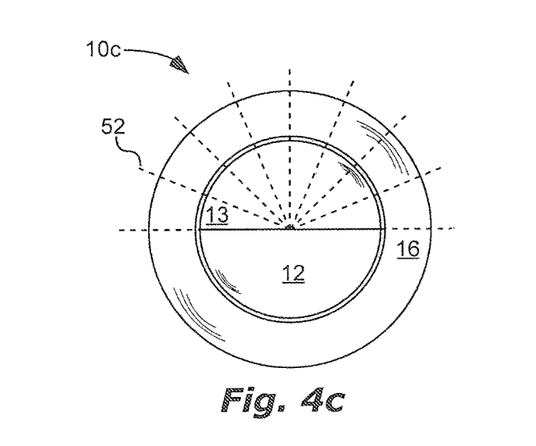
FIG. 4c is a schematic top-view of x-ray tube 10c, one embodiment of x-ray tube 10 of FIG. 1, showing emission of x-rays 52 in an approximately one-fourth spherical or $1*\pi$ steradian shape, in accordance with an embodiment of the present invention.
Figure 4D:
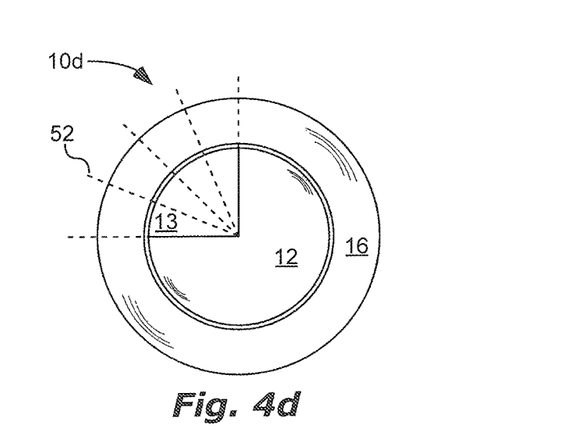
FIG. 4d is a schematic top-view of x-ray tube 10d, one embodiment of x-ray tube 10 of FIG. 1, showing emission of x-rays 52 in an approximately one-eighth spherical or $\pi/2$ steradian shape, in accordance with an embodiment of the present invention.

As shown in FIGS. 4a-4d, x-ray tube 10 can provide a hemispherical-cap or hemispherical-dome, or part of a hemispherical, emission of x-rays 52. As shown in FIG. 4b, the entire anode 12 can be the x-ray window 13 and x-ray tube 10b can provide approximately hemispherical or 2*π steradian emission of x-rays 52.

Some applications may need a more limited x-ray emission. As shown on x-ray tube 10c in FIG. 4c, about ½ of the anode 12 can be made of a material that substantially blocks x-rays, and about ½ of the anode 12 can be the x-ray window 13, thus providing an x-ray 52 emission in the shape of about one fourth spherical or 1*π steradian. As shown on x-ray tube 10d in FIG. 4d, about ¾ of the anode 12 can be made of a material that substantially blocks x-rays, and about ¼ of the anode 12 can be the x-ray window 13, thus providing an x-ray 52 emission in the shape of about one-eighth spherical or π/2 steradians. Embodiments of x-ray tube 10 include other numbers of steradians of a hemispherical-cap or hemispherical-dome emission of x-rays besides those just mentioned.

Figure 5:
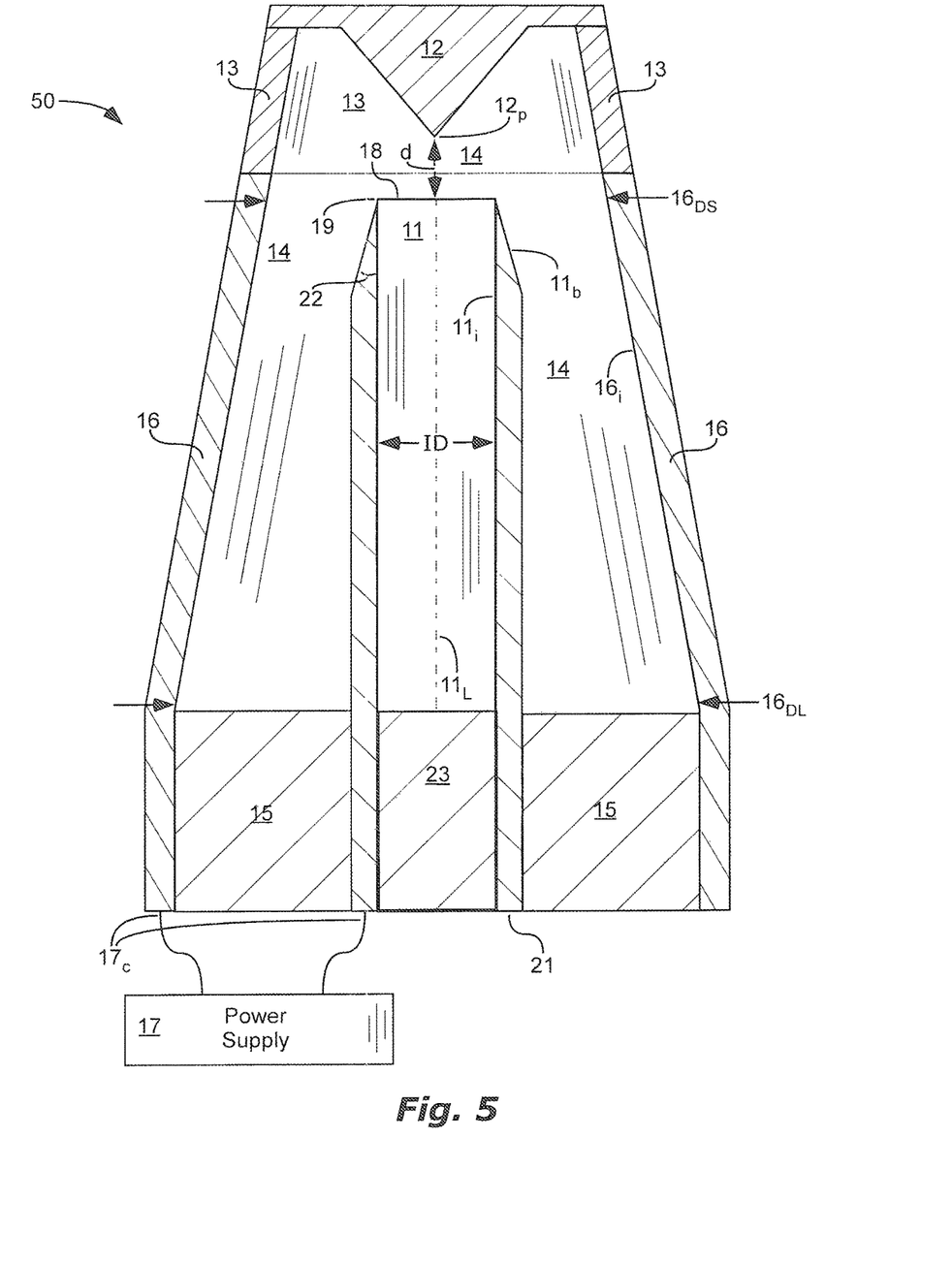
FIG. 5 is a schematic, cross-sectional side-view of a side-window x-ray tube 50 with a tube-shaped electron-emitter 11, and a power supply 17, in accordance with an embodiment of the present invention.
Figure 6A:
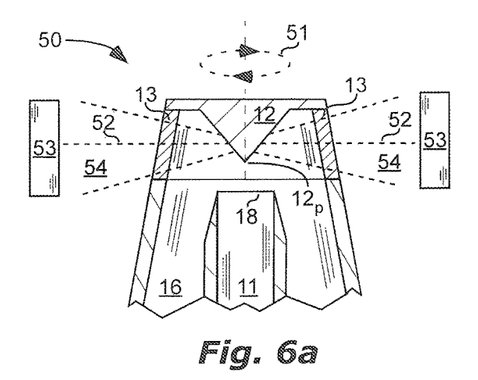
FIG. 6a is a schematic, cross-sectional side-view of a portion the x-ray tube 50 of FIG. 5, showing emission of x-rays 52 into a region-of-air 54 near a device 53 with an electrostatic charge, in accordance with an embodiment of the present invention.
Figure 6B:
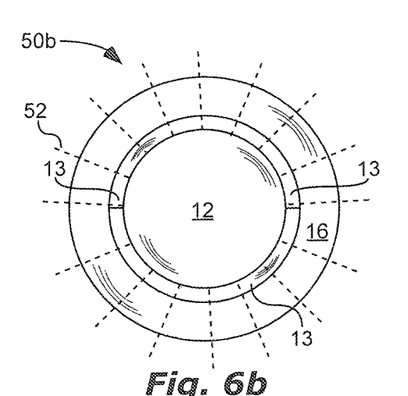
FIG. 6b is a schematic top-view of x-ray tube 50b, one embodiment of x-ray tube 50 of FIG. 5, showing emission of x-rays 52 in a 360 degree arc, radially outward from and approximately perpendicular to a longitudinal-axis $11_L$ of the electron-emitter 11, in accordance with an embodiment of the present invention.
Figure 6C:
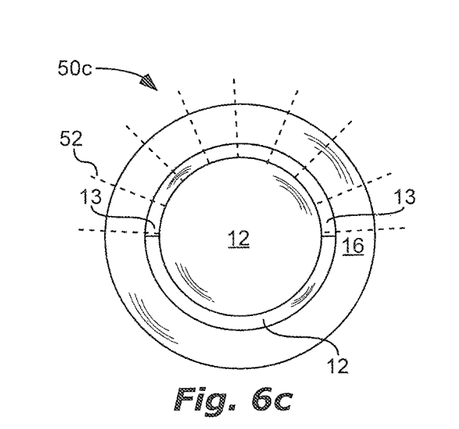
FIG. 6c is a schematic top-view of x-ray tube 50c, one embodiment of x-ray tube 50 of FIG. 5, showing emission of x-rays 52 in a 180 degree arc, radially outward from and approximately perpendicular to a longitudinal-axis $11_L$ of the electron-emitter 11, in accordance with an embodiment of the present invention.
Figure 6D:
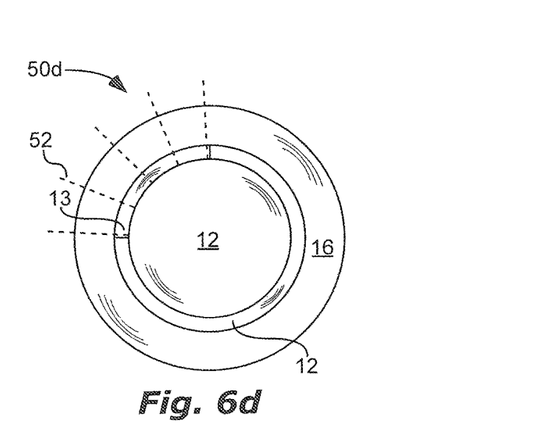
FIG. 6d is a schematic top-view of x-ray tube 50d, one embodiment of x-ray tube 50 of FIG. 5, showing emission of x-rays 52 in a 90 degree arc, radially outward from and approximately perpendicular to a longitudinal-axis $11_L$ of the electron-emitter 11, in accordance with an embodiment of the present invention.

In contrast, x-ray tube 50, shown in FIGS. 5-6d, is a side-window x-ray tube, but otherwise can have the same properties as the x-ray tube 10 described above. The anode 12 of x-ray tube 50 can include a pointed-end 12$_p$. The pointed-end 12$_p$ and/or the cone-shape can point towards the open-end 18 of the electron-emitter 11. The anode 12 of x-ray tube 50 can include a cone-shape. The anode 12 of x-ray tube 50 can include a partial cone-shape, such as for example a conical frustum. A partial cone shape can be formed by cutting the cone in half, quarter, or other portion with cutting-planes parallel to and including the height of the cone.

An outer-face of the cone-shape or partial cone-shape can include the material for generation of x-rays. The x-ray window 13 can have a curved shape and can partially or totally encircle the pointed-end $12_p$ and/or the cone-shape (or partial cone-shape). The x-ray window 13 can at least partially encircle the electron-emitter 11 and can encircle the open-end 18 of the electron-emitter 11.

As shown in FIGS. 6a-6d, depending on the extent to which the x-ray window 13 curves around or encircles the pointed-end $12_p$, the x-ray tube 50 can provide outward emission of x-rays 52 in an arc 51 radially-outward from or approximately perpendicular to the longitudinal axis $11_L$ of the electron-emitter 11 and extending outward from the pointed-end $12_p$ of the cone-shape. As shown in FIG. 6b, x-ray tube 50b, one embodiment of x-ray tube 50, can emit x-rays 52 in a 360 degree arc, radially outward from and approximately perpendicular to a longitudinal-axis $11_L$ of the electron-emitter 11.

Some applications may need limited x-ray emission, and it may be important to block x-rays from emitting in certain directions. As shown in FIG. 6c, x-ray tube 50c, one embodiment of x-ray tube 50, can emit x-rays 52 in a 180 degree arc, radially outward from and approximately perpendicular to a longitudinal-axis $11_L$ of the electron-emitter 11. The other half of the 360 degree arc can be anode with a material for blocking x-rays. As shown in FIG. 6d, x-ray tube 50d, one embodiment of x-ray tube 50, can emit x-rays 52 in a 90 degree arc, radially outward from and approximately perpendicular to a longitudinal-axis $11_L$ of the electron-emitter 11. The remaining 270 degree arc can be anode with a material for blocking x-rays. Embodiments of x-ray tube 50 include arcs with other degrees of x-ray emission, such as for example a 45 degree arc or a 270 degree arc.

Thus, x-ray tube 50, and its various embodiments 50b, 50c, and 50d can emit an arc of x-rays, as just described, but with limited steradians, such as for example greater than 0.15*pi steradians in one aspect, greater than 0.25*pi steradians in another aspect, greater than 0.5*pi steradians in another aspect, or greater than 0.9*pi steradians in another aspect; and/or less than 1.75*pi steradians in one aspect, less than 1.5*pi steradians in another aspect, or less than 1*pi steradians in another aspect. In other words, the anode 12 can substantially or totally block x-rays 52 with a trajectory that is parallel to the longitudinal axis $11_L$ of the electron-emitter 11.

Depending on the application, and the size and shape of the region of desired x-ray emission, any one of the x-ray tubes 10, 10b, 10c, 10d, 50, 50b, 50c, or 50d, may be preferred. One application for these x-ray tubes 10 and 50 is electrostatic dissipation. As shown in FIGS. 4a and 6a, x-ray tube 10 or 50 can emit x-rays 52 into a region-of-air 54 near a device 53 with an electrostatic charge, forming ions in the region-of-air 54. The ions can dissipate the electrostatic charge from the device 53.

It can be difficult to access some regions-of-air 54 near a device 53 with an electrostatic charge, due to size constraints. The x-ray tubes 10 and 50 described herein can be made relatively compact, and can be inserted into small locations.

Figure 7:
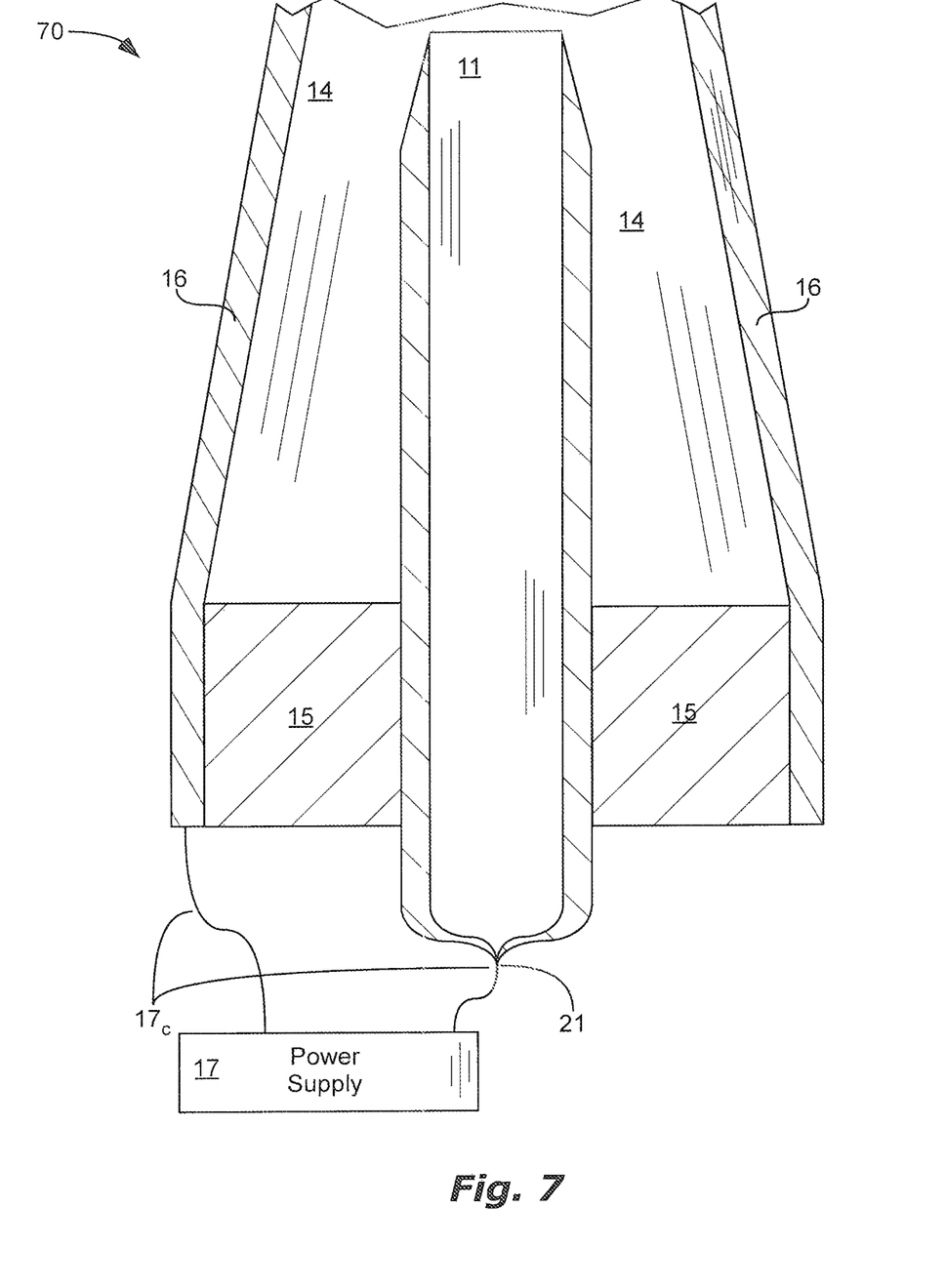
FIG. 7 is a schematic, cross-sectional side-view of a portion an x-ray tube 70 with a pinched-shut proximal-end 21 of the electron-emitter 11, in accordance with an embodiment of the present invention.

As shown on x-ray tubes 10 and 50 in FIGS. 1 and 5, an inside of the proximal-end 21 of the electron-emitter 11 can have a plug-material 23 to maintain the vacuum in the evacuated-region 14. Alternatively, as shown on the partial x-ray tube 70 in FIG. 7, the proximal-end 21 of the electron-emitter 11 can be used to draw the vacuum in the evacuated-region 14, then pinched-shut. Electrical contact can be made to the pinched-shut proximal-end 21 by various means, including by a hinge spring or a leaf spring. A pinched-shut tube for supporting an electron-emitter is described in Patent Publication Number US 2015/0071410, which is incorporated herein by reference in its entirety. X-ray tube 70 can have an x-ray window 13 and anode 12 similar to that in x-ray tube 10 or x-ray tube 50, and can have other characteristics as described above.

What is claimed is:

1. An x-ray tube comprising:
   an electron-emitter, an anode, an x-ray window, an evacuated-region between the electron-emitter and the anode, the electron-emitter electrically insulated from the anode, and the anode including a material for generation of x-rays in response to impinging electrons from the electron-emitter; and
   the electron-emitter capable of field-emission of electrons; having an open-end facing the anode with at least a portion of the evacuated-region located between the open-end and the anode; including an electrically-conductive path from an electron-emission region to an electrical connection for a power-supply; and
   the open-end of the electron-emitter having a pointed-edge with an exterior bevel.

2. An x-ray source comprising the x-ray tube of claim 1, the x-ray source further comprising:
   a power supply, the x-ray tube electrically connected to the power supply;
   the electron-emission region capable of emitting electrons to the anode, at an inside of the electron-emitter, at the open-end of the electron-emitter, or both; and
   the x-ray tube further comprising an electrically-conductive enclosure, the electrically-conductive enclosure hermetically-sealed to the anode, at least partially enclosing the evacuated-region, circumscribing at least a portion of the electron-emitter, and serving as the electrically-conductive path from the anode to the electrical connection for the power supply.

3. The x-ray tube of claim 2, wherein the electron-emitter has a proximal-end opposite of the open-end, an inner-surface of the electrically-conductive enclosure tapers inward, with a smaller inside-diameter closer to the open-end of the electron-emitter, and a larger inside-diameter closer to the proximal-end of the electron-emitter, forming a taper-angle, in order to increase an electric-field gradient at the open-end of the electron-emitter.

4. The x-ray tube of claim 2, wherein a closest solid object to the electron-emitter at the open-end is the anode.

5. The x-ray tube of claim 1, wherein the electron-emitter includes a tube-shape with a minimum inside diameter of at least 2 millimeters.

6. An x-ray tube comprising:
   a single electron-emitter;
   an anode and an x-ray window;
   an evacuated-region between the single electron emitter and the anode, the single electron-emitter being electrically insulated from the anode, and the anode including a material for generation of x-rays in response to impinging electrons from the single electron-emitter;
   the single electron-emitter: capable of field-emission of electrons; having an open-end facing the anode, with at least a portion of the evacuated-region located between the open-end and the anode; including an electron-emission region, capable of emitting electrons to the anode, at an inside of the single electron-emitter, or at the open-end of the single electron-emitter, or both; and including an electrically-conductive path from the electron-emission region to an electrical-connection for a power-supply; and a cross-section of the open-end having a pointed-edge with an exterior bevel.

7. The x-ray tube of claim 6, wherein a closest solid object to the single electron-emitter at the open-end is the anode.

8. The x-ray tube of claim 6, wherein the x-ray tube is capable of operating at less than 50° Celsius.

9. The x-ray tube of claim 6, wherein the electron-emission region has a surface area of at least 15 square millimeters.

10. The x-ray tube of claim 6, wherein the electron-emission region includes thorium, barium oxide, graphene, diamond, or combinations thereof.

11. The x-ray tube of claim 6, wherein the electron-emission region includes a material doped with arsenic, cesium, oxygen, barium, thorium, or combinations thereof.

12. The x-ray tube of claim 6, wherein the single electron-emitter includes a tube-shape with a minimum inside diameter of at least 2 millimeters.

13. The x-ray tube of claim 6, wherein the open-end has an oblique angle of between 10° and 50° with respect to a longitudinal-axis of the single electron-emitter.

14. The x-ray tube of claim 6, wherein the open-end has an oblique angle of between 45° and 75° with respect to a longitudinal-axis of the single electron-emitter.

15. The x-ray tube of claim 6, further comprising an electrically-conductive enclosure, wherein:
the electrically-conductive enclosure is hermetically-sealed to the anode, at least partially encloses the evacuated-region, and circumscribes at least a portion of the single electron-emitter;
the single electron-emitter has a proximal-end opposite of the open-end;
a portion of the single electron-emitter from the open-end towards the proximal-end for 50% of a length of the single electron-emitter defines a distal-region of the single electron-emitter; and
a first solid object, radially outward from the single electron-emitter in the distal-region, is the electrically-conductive enclosure.

16. The x-ray tube of claim 6, further comprising an electrically-conductive enclosure, wherein:
the electrically-conductive enclosure is hermetically-sealed to the anode;
the electrically-conductive enclosure at least partially encloses the evacuated-region;
the electrically-conductive enclosure circumscribes at least a portion of the single electron-emitter;
the single electron-emitter has a proximal-end opposite of the open-end; and
an inner-surface of the electrically-conductive enclosure tapers inward, with a smaller inside-diameter closer to the open-end of the single electron-emitter, and a larger inside-diameter closer to the proximal-end of the single electron-emitter, forming a taper-angle, in order to increase an electric-field gradient at the open-end of the single electron-emitter.

17. The x-ray tube of claim 16, wherein the taper-angle is between 2 degrees and 20 degrees.

18. The x-ray tube of claim 16, wherein the x-ray tube forms part of an x-ray source, the x-ray source comprising the x-ray tube electrically connected to a power supply, the electrically-conductive enclosure serving as an electrically-conductive path from the anode to an electrical connection for the power supply.

19. The x-ray tube of claim 16, wherein the x-ray tube forms part of an x-ray source, the x-ray source comprising the x-ray tube electrically connected to a power supply, the power supply providing only two bias voltages for the x-ray tube.

20. The x-ray tube of claim 6, wherein:
the single electron-emitter has a proximal-end opposite of the open-end;
a portion of the single electron-emitter from the open-end towards the proximal-end for 50% of a length of the single electron-emitter defines a distal-region of the single electron-emitter;
any straight-line-path from the single electron-emitter to the electrically-conductive enclosure, radially outward from the single electron-emitter, perpendicular to a longitudinal-axis of the single electron-emitter along the distal-region, extends only through the evacuated-region; and
a lowest voltage, radially outward from the single electron-emitter along the distal-region, is at least 3000 volts greater than a voltage of the open-end of the single electron-emitter.

* * * * *